(12) United States Patent
You et al.

(10) Patent No.: US 12,678,467 B2
(45) Date of Patent: Jul. 14, 2026

(54) MIXED BIFIDOBACTERIUM STRAIN WITH EXCELLENT PRODUCTIVITY AND ANTI-INFLAMMATORY ACTIVITY, AND USES THEREOF

(71) Applicant: LACTOMASON CO., LTD., Jinju-si (KR)

(72) Inventors: Ye Ji You, Siheung-si (KR); Je Seong Park, Seoul (KR); Gi Deok Park, Jinju-si (KR); Minn Sohn, Jinju-si (KR)

(73) Assignee: LACTOMASON CO., LTD., Jinju-si (KR)

( * ) Notice: Subject to any disclaimer, the term of this patent is extended or adjusted under 35 U.S.C. 154(b) by 0 days.

(21) Appl. No.: 19/267,709

(22) Filed: Jul. 14, 2025

(65) Prior Publication Data

US 2025/0339478 A1 Nov. 6, 2025

Related U.S. Application Data

(63) Continuation of application No. PCT/KR2024/018373, filed on Nov. 20, 2024.

(30) Foreign Application Priority Data

Apr. 25, 2024 (KR) ........................ 10-2024-0055091

(51) Int. Cl.
*A61K 35/745* (2015.01)
*A61P 29/00* (2006.01)

(52) U.S. Cl.
CPC ............ *A61K 35/745* (2013.01); *A61P 29/00* (2018.01)

(58) Field of Classification Search
CPC .............................. A61K 35/745; A61P 29/00
See application file for complete search history.

(56) References Cited

FOREIGN PATENT DOCUMENTS

| | | |
|---|---|---|
| KR | 10-2014-0037545 A | 3/2014 |
| KR | 10-1611830 B1 | 4/2016 |
| KR | 10-2040117 B1 | 11/2019 |
| KR | 10-2136346 B1 | 7/2020 |
| KR | 10-2296285 B1 | 9/2021 |
| KR | 10-2559527 B1 | 7/2023 |

OTHER PUBLICATIONS

Choi et al., J. Microbiol. Biotechnol. 2022. 32(9): 1186-1194. doi.org/10.4014/jmb.2206.06023. (Year: 2022).*
Amway Korea, "Balance within immunity", List of ingredients and content; description of function. Jan. 5, 2021 (Release date), [URL:https://www.amway.co.kr/shop/nutrition/basic/probiotic-fibers/p/303426K].

* cited by examiner

*Primary Examiner* — Kade Ariani
(74) *Attorney, Agent, or Firm* — NKL LAW; Jae Youn Kim

(57) ABSTRACT

Provided is a mixed strain with both excellent anti-inflammatory activity and excellent productivity, including *Bifidobacterium animalis* subsp. *lactis* LM1017 (Accession No. KCCM12629P), *Bifidobacterium breve* LM1092 (Accession No. KCCM13464P), *Bifidobacterium longum* LM1024 (Accession No. KCCM12919P), and *Bifidobacterium bifidum* LM1108 (Accession No. KCCM13463P). The strain provided herein has an excellent commercial viability of probiotics.

7 Claims, 2 Drawing Sheets

MIXED BIFIDOBACTERIUM STRAIN WITH EXCELLENT PRODUCTIVITY AND ANTI-INFLAMMATORY ACTIVITY, AND USES THEREOF

TECHNICAL FIELD

The present disclosure relates to a mixed *Bifidobacterium* strain with both excellent productivity and excellent anti-inflammatory activity, and to uses thereof.

BACKGROUND

Lactic acid bacteria have been consumed by humans throughout history, and as a microorganism exhibiting highly beneficial effects on human health, the usefulness of this group of bacteria appears to be higher now than ever before. With extensive investigations in recent years, huge progress has been made in the understanding and application of lactic acid bacteria, and they are used in a broad application range, i.e., new drugs and health products as well as common food products are developed. Selected strains of lactic acid bacteria colonize the intestine of animals, decompose nutrients and various carbohydrates that are taken by the animals to use them as an energy source, and produce lactic acid and antimicrobial materials to protect the intestine, also by way of competition, against the growth of harmful bacteria. Accordingly, they contribute greatly to maintaining the intestinal health. Also, lactic acid bacteria strains are widely used to promote animal growth, improve feed utilization and conversion, increase resistance to diseases, suppress growth of harmful bacteria, reduce mortality, suppress production of toxic substances, and produce various vitamins. However, to exhibit the effects as described above, the viable lactic acid bacteria must arrive in the intestine from the outside in a viable condition without any interruption. In order to exhibit their function properly in the intestine, the destruction of lactic acid bacteria by gastric acid, which is secreted following oral administration, should be minimal while strong resistance to bile acid should be exhibited.

Inflammation occurs when an organism's immune system attempts to defend harmful substances such as invasive pathogens. Immunomodulatory mechanisms, including immunomodulatory cells, cytokines and apoptosis, regulate immune responses caused by an overreaction to defend against pathogens. The deficiency of the immunomodulatory mechanisms manifests various inflammatory diseases including inflammatory bowel disease (IBD). The production of cytokines triggered by bacterial components such as lipopolysaccharides (LPS), lipoteichoic acid (LTA), and peptidoglycan can lead to systemic inflammatory response syndrome. LPS activates cells of the innate immune system to produce various proinflammatory cytokines, such as interleukin-1 (IL-1), IL-6, IL-8, and TNF-$\alpha$, as well as nitric oxide (NO). NO is a highly reactive molecule generated from L-arginine by the family of NO synthases (NOS) isoenzymes. The isoenzymes present in macrophages are the inducible form (inducible NOS, iNOS), which can produce high concentrations of NO in various cells upon stimulation by bacterial endotoxins, LPS, or other proinflammatory cytokines including TNF-$\alpha$, IFN-$\gamma$, IL-1, and IL-6. Among several inflammatory diseases, inflammatory bowel diseases (IBD) are closely associated with lactic acid bacteria. Patients with IBD may experience abdominal pain, diarrhea, intestinal obstruction, and/or bloody stool. To date, anti-inflammatory agents, steroids, or anti-TNF agents have been known to effectively alleviate symptoms. However, a fundamental medical cure for IBD has not yet been identified.

DISCLOSURE OF THE INVENTION

Problems to be Solved by the Invention

The present inventors combined four strains belonging to the genus *Bifidobacterium* by adding *Bifidobacterium breve* LM1092, which exhibits low anti-inflammatory activity but excellent productivity like strain LM1017, and *Bifidobacterium bifidum* LM1108, which exhibits high anti-inflammatory activity but low productivity like strain LM1024, to the strains LM1017 and LM1024. Through this combination, the inventors provide a mixed strain with both excellent anti-inflammatory activity and excellent productivity, as well as uses thereof.

Means for Solving the Problems

An aspect of the present disclosure provides a mixed strain with both excellent anti-inflammatory activity and excellent productivity, including *Bifidobacterium animalis* subsp. *lactis* LM1017 (Accession No. KCCM12629P), *Bifidobacterium breve* LM1092 (Accession No. KCCM13464P), *Bifidobacterium longum* LM1024 (Accession No. KCCM12919P), and *Bifidobacterium bifidum* LM1108 (Accession No. KCCM13463P).

The mixed strain of the present disclosure can be utilized as a probiotic, and more specifically, it can be used as an active ingredient in an anti-inflammatory composition, a food composition, a health functional food composition, or a pharmaceutical composition, in the form of the mixed strain itself, a culture of the mixed strain, a lysate of the mixed strain, or an extract of the mixed strain, individually or in combination.

Another aspect of the present disclosure provides a method of improving anti-inflammatory activity, including a process of administering to a subject in need thereof one or more of a mixed strain of the present disclosure, a culture of the mixed strain, a lysate of the mixed strain, and an extract of the mixed strain.

Yet another aspect of the present disclosure provides a use of one or more of a mixed strain of the present disclosure, a culture of the mixed strain, a lysate of the mixed strain, and an extract of the mixed strain to improve anti-inflammatory activity and productivity.

Still another aspect of the present disclosure provides a use of one or more of a mixed strain of the present disclosure, a culture of the mixed strain, a lysate of the mixed strain, and an extract of the mixed strain to produce an anti-inflammatory pharmaceutical agent.

Effects of the Invention

The effects of the present disclosure include not only high anti-inflammatory activity but also excellent productivity, resulting in excellent commercial viability of probiotics.

BEST MODE FOR CARRYING OUT THE INVENTION

Figure 1:
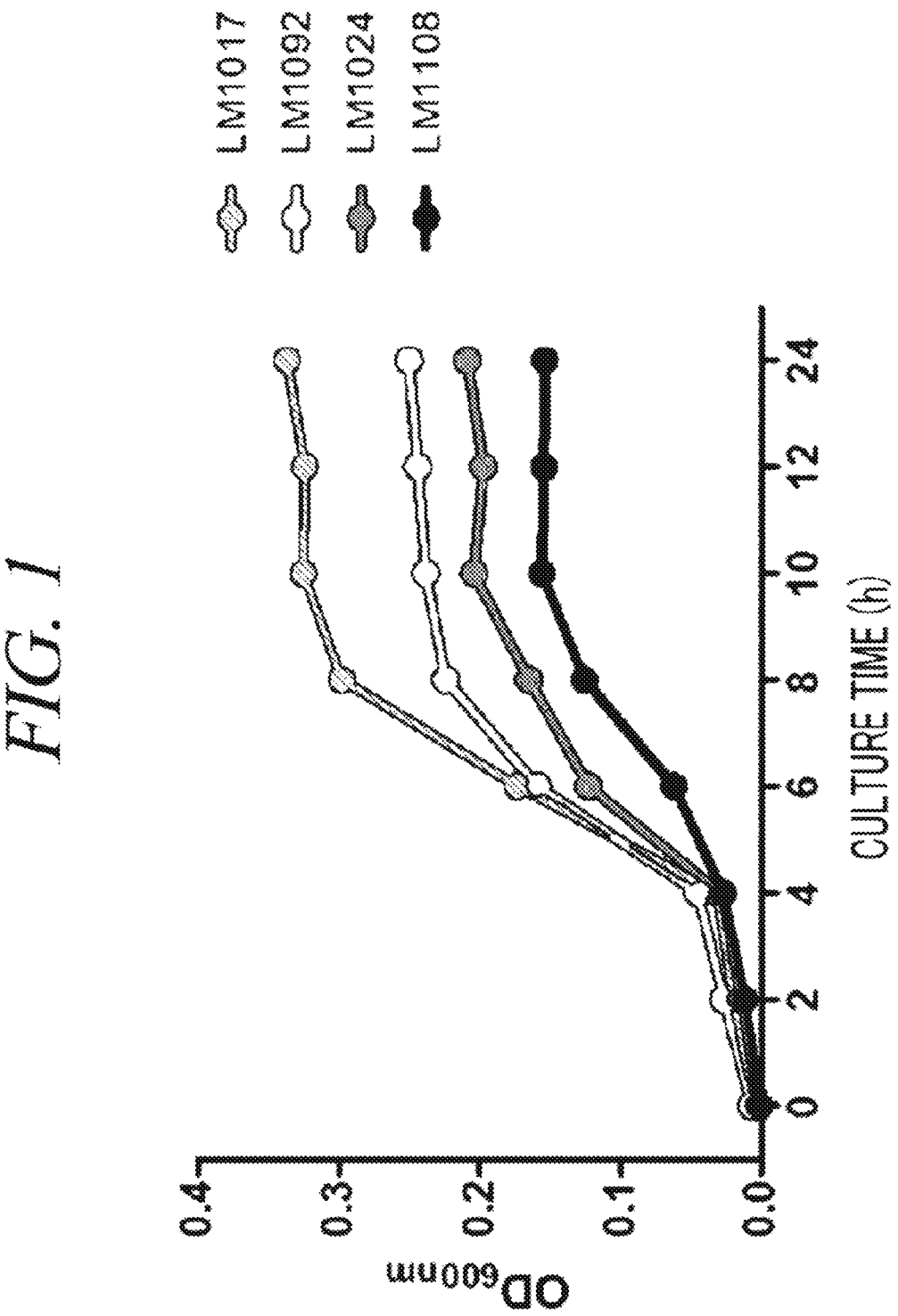
FIG. 1 shows the results of productivity tests according to Example 1.

Hereafter, embodiments will be described in detail with reference to the accompanying drawings so that the present disclosure may be readily implemented by a person with ordinary skill in the art. However, it is to be noted that the present disclosure is not limited to the embodiments but can be embodied in various other ways. In the drawings, parts irrelevant to the description are omitted for the simplicity of explanation, and like reference numerals denote like parts throughout the whole document.

Throughout the whole document, the term "comprises or includes" and/or "comprising or including" used in the document means that one or more other components, steps, operation and/or existence or addition of elements are not excluded in addition to the described components, steps, operation and/or elements unless context dictates otherwise.

Throughout the whole document, the term "step of" does not mean "step for".

Throughout the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the whole document, a phrase in the form "A and/or B" means "A or B, or A and B".

Throughout the whole document, the term "*Bifidobacterium animalis* subsp. *lactis* LM1017" refers to strain *Bifidobacterium animalis* subsp. *lactis* LM1017, and may also be referred to as LM1017 or strain LM1017.

Throughout the whole document, the term "*Bifidobacterium breve* LM1092" refers to strain *Bifidobacterium breve* LM1092, and may also be referred to as LM1092 or strain LM1092.

Throughout the whole document, the term "*Bifidobacterium longum* LM1024" refers to strain *Bifidobacterium longum* LM1024, and may also be referred to as LM1024 or strain LM1024.

Throughout the whole document, the term "*Bifidobacterium bifidum* LM1108" refers to strain *Bifidobacterium bifidum* LM1108, and may also be referred to as LM1108 or strain LM1108.

Each of the strains can be interpreted to include a strain itself, a culture of the strain, a lysate of the strain, an extract of the strain, and a cytoplasmic fraction obtained by lysing the strain.

In an embodiment, the strain may be a mutant of a naturally occurring strain.

In an embodiment, the strain may be a mixed strain that exhibits both excellent anti-inflammatory activity and excellent productivity. The anti-inflammatory activity may include the inhibition of nitric oxide production.

Throughout the whole document, the term "culture" refers to an entire medium including the strain itself, an extract of the strain, metabolites of the strain, or extra nutrients obtained by culturing the strain for a certain period of time on a nutrient medium. It also includes a culture solution from which the strain was removed after culturing. Further, it may include a concentrate of the entire medium or culture solution, and a dried product of the concentrate. Specifically, the culture of the present disclosure can use a medium easily selected by a person with ordinary skill in the art depending on the desired purpose among the media used for microbial culture, for example, a de Man-Rogosa and Sharpe (MRS) medium or a BL medium. However, it is not limited thereto as long as the strain of the present disclosure can be cultured.

Throughout the whole document, the term "lysate" may be used interchangeably with "crushed product", and may refer to a solution or suspension in an aqueous medium of cells of a microorganism such as a strain that has been crushed. A cell lysate includes, for example, macromolecules, such as DNA, RNA, proteins, peptides, carbohydrates, or lipids, and/or micromolecules, such as amino acids, sugars, or fatty acids, or fractions thereof. The lysate also includes cell debris, which may be smooth or have a granular structure.

Throughout the whole document, the term "extract" refers to a material isolated from the culture medium of the strain. The extract may also include fractions or a culture filtrate.

In general, strains used as probiotics are expected to exhibit the same or similar effects whether in the form of the strain itself, a culture of the strain, a lysate of the strain, or an extract of the strain.

Throughout the whole document, the term "productivity" refers to the productivity of the strain, and may relate to the number of strains obtainable after culturing. For example, excellent productivity of a strain may mean that a greater number of strains can be obtained after culturing. In the probiotics industry, the productivity of lactic acid bacteria directly affects the productivity of probiotic products. Therefore, the productivity of the strain is directly connected to the commercial viability of probiotics. Accordingly, it is important to use a strain that not only has beneficial functions but also exhibits excellent productivity.

Further, throughout the whole document, the expression "excellent productivity" means that it facilitates the obtaining of the required amount of lactic acid bacteria for probiotic products. It does not imply that the productivity of strains cultured together is greater than that of the individual strains cultured separately. That is, the excellent productivity of the present disclosure means that it is easier to obtain the required amount of lactic acid bacteria for probiotic products by using a combination of high productivity strains and low productivity strains than by using only low productivity strains, but does not mean that culturing the mixed strain in a single medium produces a better result.

Throughout the whole document, the term "logarithmic phase" refers to the phase in the bacterial growth curve where a microbial population doubles.

Throughout the whole document, the term "stationary phase" refers to the phase in the bacterial growth curve where a microbial population ceases to grow and the growth curve plateaus.

Throughout the whole document, the term "food" may include meats, sausages, breads, chocolates, candies, snacks, confectionery, pizza, ramens, other noodles, gums, dairy products including ice cream, soups, beverages, teas, drinks, alcohol drinks, vitamin complexes, health functional foods and health foods, and may include all foods in the accepted meaning, such as natural foods and processed foods.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time, and may have excellent portability. Therefore, the food of the present disclosure may be taken as a supplement.

The food composition may further contain a physiologically acceptable carrier. The kind of the carrier is not particularly limited. Any carrier may be used as long as it is commonly used in the art.

Moreover, the food composition may contain additional ingredients that are commonly used in food compositions to improve smell, taste, visual appearance, and the like. For example, it may contain vitamins A, C, D, E, B1, B2, B6, B12, K1, K2, niacin, biotin, folate, pantothenic acid, and the like. It may also contain minerals, such as zinc (Zn), iron (Fe), calcium (Ca), chromium (Cr), magnesium (Mg), manganese (Mn), copper (Cu), and the like.

The food composition of the present disclosure may be used as, for example, a health beverage composition, and in this case, the health beverage composition may further contain various natural carbohydrates or sweeteners, as in common beverages. The natural carbohydrates may include monosaccharides, disaccharides, polysaccharides, and sugar alcohols. The sweeteners may be natural sweeteners, such as thaumatin, a *stevia* extract, xylitol, allulose, inulin, etc.; or synthetic sweeteners, such as saccharin, aspartame, sucralose, etc.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols, carbonating agents, etc. Moreover, the health beverage composition may contain fruit flesh used to prepare natural fruit juices, fruit juice beverages, or vegetable beverages. These ingredients may be used individually or in combination.

Throughout the whole document, the term "health functional food" refers to foods prepared and processed using raw materials or ingredients having useful functions in accordance with Korean Health Functional Foods Act, No. 6727, and the term "functionality" refers adjusting nutrients on a structure and a function of the human body or obtaining a useful effect for health such as a physiological action.

The health functional food refers to a food having effects of actively maintaining or promoting health conditions, as compared with general foods, and a health supplement food refers to a food for supplementing health. If necessary, the health functional food, health food, and health supplement food may be interchangeably used with each other. Specifically, the health functional food is a food prepared by adding the strain of the present disclosure to food materials, such as beverages, teas, spices, gums, confectionery, etc., or prepared in a capsule, powder or suspension form. The health functional food means that it has a specific effect on health when consumed, but unlike general drugs, the health functional food is free from side effects that may occur when a drug is taken for a long time since the food is used as raw materials.

Throughout the whole document, the pharmaceutical composition may be formulated and used in the form of oral medications, such as powders, granules, tablets, capsules, suspensions, emulsions, syrups or aerosols, ointments, suppositories or sterile injection solutions by conventional methods, respectively, but may not be limited thereto.

The pharmaceutical composition according to an embodiment of the present disclosure may be a drug composition or a quasi-drug composition.

Throughout the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

In an embodiment of the present disclosure, the pharmaceutical composition may be administered in a pharmaceutically effective amount. Throughout the whole document, the term "pharmaceutically effective amount" refers to an amount sufficient to treat or prevent diseases at a reasonable benefit or risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with a known ingredient for treating intestinal diseases. It is important to administer an amount to obtain a maximum effect in a minimum amount without side effects by considering all of the above-described factors.

The pharmaceutical composition of the present disclosure may be administered through routes, including intraperitoneal, intravenous, intramuscular, subcutaneous, intradermal, transdermal patch, oral, intranasal, intrapulmonary, and intrarectal administration routes, depending on the purpose, without being particularly limited thereto. However, the pharmaceutical composition may be administered orally in an unformulated form, and since the pharmaceutical composition of the present disclosure can be denatured or decomposed by gastric acid, the active ingredient of the composition for oral administration may be coated or the composition may be administered orally in a formulated form or an oral patch form so as to be protected from degradation in the stomach. In addition, the composition may also be administered using any device capable of delivering the active ingredient to target cells.

Hereinafter, embodiments and examples of the present disclosure will be explained in detail with reference to the accompanying drawings. However, the present disclosure may not be limited to these embodiments, examples, and drawings.

The present disclosure provides a mixed strain with both excellent anti-inflammatory activity and excellent productivity, including *Bifidobacterium animalis* subsp. *lactis* LM1017 (Accession No. KCCM12629P), *Bifidobacterium breve* LM1092 (Accession No. KCCM13464P), *Bifidobacterium longum* LM1024 (Accession No. KCCM12919P), and *Bifidobacterium bifidum* LM1108 (Accession No. KCCM13463P).

Under the provisions of the Budapest Treaty on the International Recognition of the Deposit of Microorganisms for the Purposes of Patent Procedure, the *Bifidobacterium animalis* subsp. *lactis* LM1017 strain was deposited with the international depositary authority, the Korean Culture Center of Microorganisms, on Nov. 14, 2019, under the Accession Number KCCM12629P, the *Bifidobacterium longum* LM 1024 strain was deposited with the international depositary authority, the Korean Culture Center of Microorganisms, on Dec. 23, 2020, under the Accession Number KCCM12919P, the *Bifidobacterium bifidum* LM1108 strain was deposited with the international depositary authority, the Korean Culture Center of Microorganisms, on Mar. 29, 2024, under the Accession Number KCCM13463P, and the *Bifidobacterium breve* LM1092 strain was deposited with the international depositary authority, the Korean Culture Center of Microorganisms, on Mar. 29, 2024, under the Accession Number KCCM13464P.

The present inventors mixed the strains LM1017 and LM1024 previously known for their anti-inflammatory effects with the strains LM1092 and LM1108 in order to identify a mixed strain that exhibits both excellent anti-inflammatory activity and excellent productivity.

In an embodiment of the present disclosure, a mixing ratio of the strains (LM1017 and LM1092 [Group A]: LM1024 and LM1108 [Group B]) may preferably be in the range of 32:1 to 8:1, 32:1 to 1:1, 32:1 to 1:8, 32:1 to 1:32, 8:1 to 1:1, 8:1 to 1:8, 8:1 to 1:32, 1:1 to 1:8, 1:1 to 1:32, or 1:8 to 1:32, but is not limited thereto.

In an embodiment of the present disclosure, the anti-inflammatory activity may include the inhibition of nitric oxide production.

The present disclosure provides a composition containing, as an active ingredient, one or more of the mixed strain, a culture of the mixed strain, a lysate of the mixed strain, and an extract of the mixed strain. The composition may be an anti-inflammatory composition, an anti-inflammatory food composition, an anti-inflammatory health functional food composition, or an anti-inflammatory pharmaceutical composition.

In an embodiment of the present disclosure, the characteristics of the mixed strain contained in the above-described compositions may be the same as those described above for the mixed strain.

Another aspect of the present disclosure provides a method of improving anti-inflammatory activity, including a process of administering to a subject in need thereof one or more of the mixed strain, a culture of the mixed strain, a lysate of the mixed strain, and an extract of the mixed strain.

Yet another aspect of the present disclosure provides a use of one or more of the mixed strain, a culture of the mixed strain, a lysate of the mixed strain, and an extract of the mixed strain to improve anti-inflammatory activity and productivity.

Still another aspect of the present disclosure provides a use of one or more of the mixed strain, a culture of the mixed strain, a lysate of the mixed strain, and an extract of the mixed strain to produce a pharmaceutical agent for improving anti-inflammatory activity.

Based on the evaluation result of anti-inflammatory activity and productivity of each strain used in the mixed strain of the present disclosure, it was found that the strains LM1017 and LM1092 individually showed low anti-inflammatory activity and excellent productivity, whereas the strains LM1024 and LM1108 individually showed high anti-inflammatory activity and low productivity. However, by mixing all of the above-described strains, the low productivity of the strains LM1024 and LM1108 was improved. As a result of checking the anti-inflammatory activity of the mixed strain, it was found to be excellent. Based on these findings, the present disclosure was completed.

MODE FOR CARRYING OUT THE INVENTION

Example 1. Test to Confirm Productivity

A test was conducted to confirm the productivity of strains *Bifidobacterium animalis* subsp. *lactis* LM1017, *Bifidobac-*

*terium breve* LM1092, *Bifidobacterium longum* LM1024, and *Bifidobacterium bifidum* LM1108.

Each strain was precultured once (37° C., 18 hours) in BL liquid medium (BL broth). Subsequently, 1% of strains were inoculated into the same medium and subjected to static culture at 37° C. The productivity of each strain was determined based on an optical density (OD) of the culture solution at 600 nm ($OD_{600nm}$) by performing a turbidity measurement method after 0, 2, 4, 6, 8, 10, 12, and 24-hour culture.

As a result, it was confirmed that the $OD_{600nm}$ was increased in the order of *Bifidobacterium bifidum* LM1108, *Bifidobacterium longum* LM1024, *Bifidobacterium breve* LM1092, and *Bifidobacterium animalis* subsp. *lactis* LM1017 during the logarithmic and stationary phases (see FIG. 1 and Table 1).

Accordingly, it was confirmed that the productivity of the strains LM1017 and LM1092 was about twice as high as that of the strains LM1024 and LM1108 (based on culture time of 6 hours). However, the present inventors improved the low productivity of the strains LM1024 and LM1108 by mixing them with the strains LM1017 and LM1092.

TABLE 1

| Culture time | $OD_{600\ nm}$ | | | |
| --- | --- | --- | --- | --- |
| (h) | LM1017 | LM1092 | LM1024 | LM1108 |
| 0 | 0.0050 | 0.0070 | 0.0030 | 0.0010 |
| 2 | 0.0197 | 0.0269 | 0.0162 | 0.0120 |
| 4 | 0.0314 | 0.0452 | 0.0290 | 0.0270 |
| 6 | 0.1736 | 0.1595 | 0.1232 | 0.0621 |
| 8 | 0.2980 | 0.2240 | 0.1650 | 0.1258 |
| 10 | 0.3253 | 0.2386 | 0.2043 | 0.1563 |
| 12 | 0.3242 | 0.2443 | 0.1974 | 0.1545 |
| 24 | 0.3367 | 0.2504 | 0.2089 | 0.1541 |

Example 2. Test to Confirm Anti-Inflammatory Activity

A test was conducted to confirm the anti-inflammatory activity of a mixed strain including *Bifidobacterium animalis* subsp. *lactis* LM1017, *Bifidobacterium breve* LM1092, *Bifidobacterium longum* LM1024, and *Bifidobacterium bifidum* LM1108. The anti-inflammatory activity was assessed based on the inhibition of nitric oxide (NO) production.

Specifically, a DMEM medium (Welgene, Korea) made of 10% fetal bovine serum (FBS) (Welgene, Korea) and penicillin-streptomycin (Welgene, Korea) was used to culture RAW 264.7 cells, which are a murine macrophage cell line. The RAW 264.7 cells were seeded in a 96-well plate at a concentration of $3 \times 10^4$ cells/well and then cultured overnight (O/N) in a 37° C., $CO_2$ incubator. After removing the medium from each well, *Bifidobacterium animalis* subsp. *lactis* LM1017, *Bifidobacterium breve* LM1092, *Bifidobacterium longum* LM1024, and *Bifidobacterium bifidum* LM1108 were diluted in the medium and treated either individually or in combination for 2 hours. To induce inflammation in the RAW 264.7 cells, lipopolysaccharide (LPS) was added to each well, followed by an additional 24-hour culture in a 37° C., $CO_2$ incubator. To measure NO production, the Griess Reagent System (Promega) was used. 50 µL of the cultured supernatant was transferred to a new 96-well plate. An NO standard curve was generated using an NO standard solution diluted to concentrations ranging from 1.56 µM to 100 µM. Then, 50 µL of a sulfanilamide solution was added to each well, followed by a 5-minute reaction at room temperature in the dark. Afterwards, 50 µL of an NED solution was added to each well, and the plate was incubated in the dark for another 5 minutes at room temperature.

Absorbance was measured at 540 nm using a microplate reader, and the NO production was calculated based on the NO standard curve.

First, the NO inhibition capacity of each individual strain was examined. The results showed that *Bifidobacterium animalis* subsp. *lactis* LM1017, *Bifidobacterium breve* LM1092 each exhibited approximately 5% inhibition of NO production induced by inflammation caused by LPS, LM1024 exhibited approximately 11% inhibition of NO production, and LM1108 exhibited approximately 16% inhibition of NO production (see FIG. 2 and Table 2, Left panel). That is, it was confirmed that the strains LM1017 and LM1092 exhibited relatively low anti-inflammatory activity, whereas the strains LM1024 and LM1108 exhibited higher anti-inflammatory activity.

Figure 2:
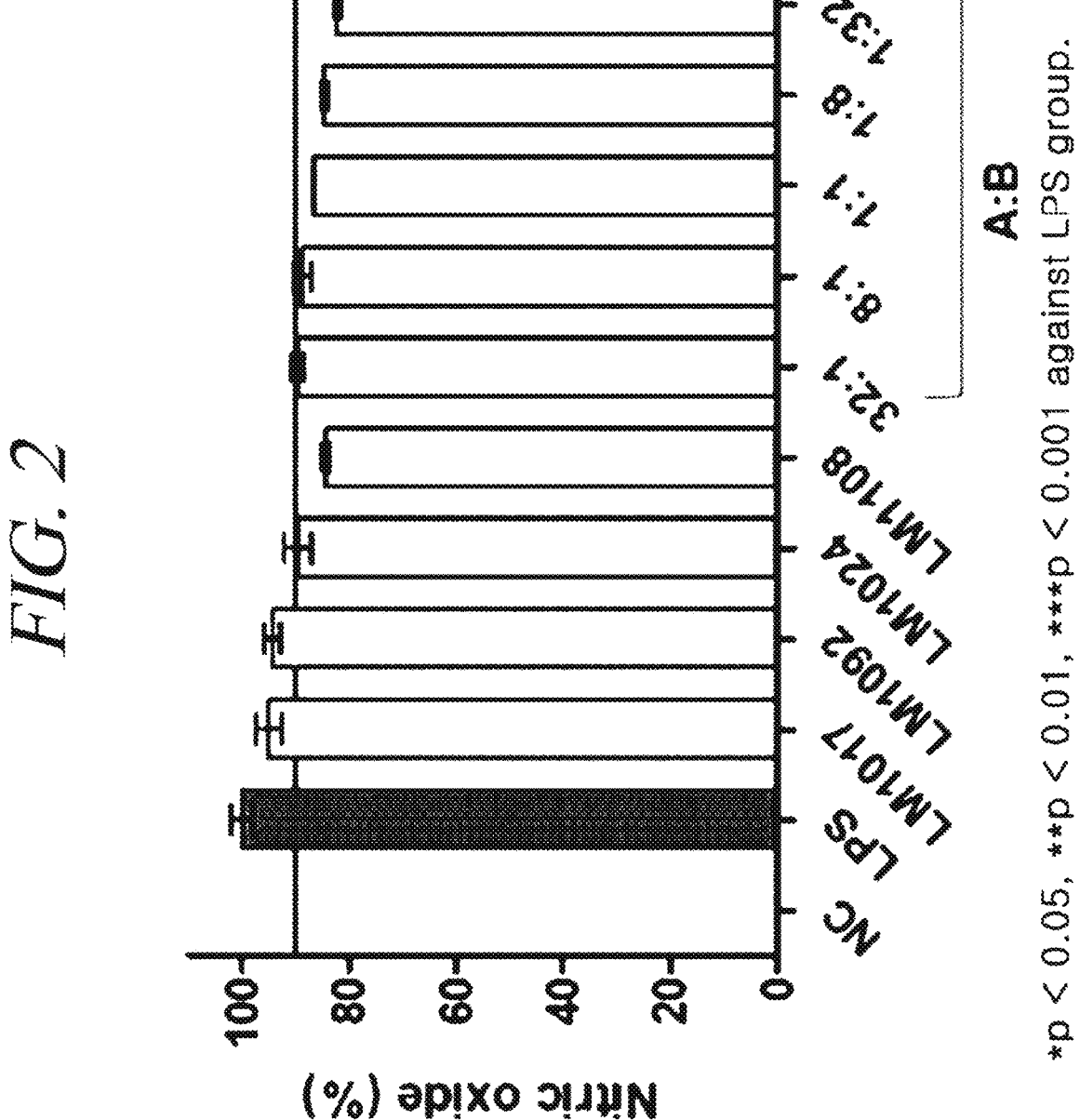
FIG. 2 shows the results of anti-inflammatory activity tests according to Example 2.

To develop a probiotic with enhanced productivity, the present inventors mixed all of the above-described four strains. The strains were grouped into Group A (strains LM1017 and LM1092, which have excellent productivity) and Group B (strains LM1024 and LM1108, which have high anti-inflammatory activity). To assess the influence of each group on the anti-inflammatory activity of the mixed strain, the Groups A and B were mixed at various mixing ratios to prepare mixed strains, and the NO inhibition capacity of each mixed strain was evaluated (see FIG. 2 and Table 2, Right panel; A:B). The horizontal line shown in FIG. 2 represents the threshold for 90% NO inhibition capacity, which indicates the standard level of anti-inflammatory activity required for commercialization.

As a result, all of the mixed strains exhibited at least 10% NO inhibition capacity, regardless of the A:B mixing ratio, and the experimental values were about 5% to 7% lower than the theoretical values. This confirms a synergistic effect in NO inhibition when using the four strains according to the present disclosure. In particular, in all mixing ratios, the mixed strain exhibited excellent NO inhibition capacity compared to the individual strains LM1017 and LM1092, which are high in productivity only. These findings indicate that the mixed strain of the present disclosure successfully overcomes the limitations of individual strains with low anti-inflammatory activity or low productivity, and exhibits both excellent anti-inflammatory activity and excellent productivity.

TABLE 2

| | Nitric oxide (%) | Theoretical value [1] | Experimental value/ Theoretical value |
|---|---|---|---|
| Negative control group | 0.00 | — | — |
| LPS-treated group (Positive control group) | 100.00 | — | — |

TABLE 2-continued

| | | Nitric oxide (%) | Theoretical value [1] | Experimental value/ Theoretical value |
|---|---|---|---|---|
| Single treatment group | LM1017 | 95.04 | — | — |
| | LM1092 | 94.38 | — | — |
| | LM1024 | 89.45 | — | — |
| | LM1108 | 84.40 | — | — |
| A:B | 32:1 | 89.69 | 94.80 | 0.95 |
| | 8:1 | 88.68 | 94.27 | 0.94 |
| | 1:1 | 86.63 | 91.70 | 0.94 |
| | 1:8 | 84.65 | 89.14 | 0.95 |
| | 1:32 | 82.16 | 88.61 | 0.93 |

[1] Theoretical values: Calculated based on NO levels of single treatments according to the mixing ratio.

We claim:

1. A mixed strain with both excellent anti-inflammatory activity and excellent productivity, comprising:
   *Bifidobacterium animalis* subsp. *lactis* LM1017 deposited with the Korean Culture Center of Microorganisms under Accession No. KCCM12629P;
   *Bifidobacterium breve* LM1092 deposited with the Korean Culture Center of Microorganisms under Accession No. KCCM13464P;
   *Bifidobacterium longum* LM1024 deposited with the Korean Culture Center of Microorganisms under Accession No. KCCM12919P; and
   *Bifidobacterium bifidum* LM1108 deposited with the Korean Culture Center of Microorganisms under Accession No. KCCM13463P,
   wherein a mixing ratio of the mixed strain is 32:1 to 1:32 based on "LM1017 and LM1092":"LM1024 and LM1108".

2. The mixed strain of claim 1,
   wherein the anti-inflammatory activity includes the inhibition of nitric oxide production.

3. An anti-inflammatory composition containing the mixed strain of claim 1, a culture thereof, a lysate thereof, an extract thereof, or a combination thereof as an active ingredient.

4. An anti-inflammatory food composition containing the mixed strain of claim 1, a culture thereof, a lysate thereof, and an extract thereof, or a combination thereof as an active ingredient.

5. An anti-inflammatory health functional food composition containing the mixed strain of claim 1, a culture thereof, a lysate thereof, an extract thereof, or a combination thereof as an active ingredient.

6. An anti-inflammatory pharmaceutical composition containing the mixed strain of claim 1, a culture thereof, a lysate thereof, an extract thereof, or a combination thereof as an active ingredient.

7. A method of improving anti-inflammatory activity, comprising:
   a process of administering to a subject in need thereof the mixed strain of claim 1, a culture thereof, a lysate thereof, an extract thereof, or a combination thereof.

\* \* \* \* \*